(12) United States Patent
Tang

(10) Patent No.: US 7,980,147 B2
(45) Date of Patent: Jul. 19, 2011

(54) MULTIGAS PASSIVE SAMPLER

(76) Inventor: Hongmao Tang, Edmonton (CA)

( * ) Notice: Subject to any disclaimer, the term of this patent is extended or adjusted under 35 U.S.C. 154(b) by 0 days.

(21) Appl. No.: 12/487,990

(22) Filed: Jun. 19, 2009

(65) Prior Publication Data

US 2009/0301229 A1   Dec. 10, 2009

Related U.S. Application Data

(63) Continuation-in-part of application No. 12/143,260, filed on Jun. 20, 2008.

(60) Provisional application No. 60/945,119, filed on Jun. 20, 2007.

(51) Int. Cl.
*G01N 1/22* (2006.01)
(52) U.S. Cl. ............... 73/863.25; 73/863.21; 73/863.31
(58) Field of Classification Search ... 73/863.21–863.31
See application file for complete search history.

(56) References Cited

U.S. PATENT DOCUMENTS

| | | | | |
|---|---|---|---|---|
| 3,495,458 A | * | 2/1970 | Christensen | 73/863.24 X |
| 4,758,521 A | * | 7/1988 | Lushbaugh et al. | 73/863.21 X |
| 5,081,871 A | * | 1/1992 | Glaser | 73/863.23 |
| 5,308,483 A | * | 5/1994 | Sklar et al. | 73/863.23 X |
| 5,574,230 A | * | 11/1996 | Baugh | 73/863.23 |
| 5,898,114 A | * | 4/1999 | Basch et al. | 73/863.23 |
| 6,607,581 B2 | * | 8/2003 | Smith et al. | 73/863.21 X |
| 7,059,206 B1 | * | 6/2006 | Kingston et al. | 73/863.23 |
| 7,073,402 B2 | * | 7/2006 | Trakumas et al. | 73/863.22 |
| 7,559,980 B2 | * | 7/2009 | Guild | 73/863.23 X |
| 7,597,015 B2 | * | 10/2009 | Harley | 73/865.5 |
| 2008/0078289 A1 | * | 4/2008 | Sergi et al. | 73/863.23 X |

FOREIGN PATENT DOCUMENTS

| | | | | |
|---|---|---|---|---|
| EP | 1329714 A1 | * | 7/2003 | |
| EP | 1655594 A1 | * | 5/2006 | |
| JP | 58195135 A | * | 11/1983 | 73/863.25 |
| JP | 02024534 A | * | 1/1990 | 73/863.23 |
| JP | 2002005797 A | * | 1/2002 | |
| JP | 2003185541 A | * | 7/2003 | |
| WO | WO 2005057177 A1 | * | 6/2005 | |

OTHER PUBLICATIONS

Koutrakis, P et al.; Measurement of ambient ozone using a nitrite coated filter: Anal. Chem., (1993) 65, 209-214, p. 209 only provided.
Krupa, S.V. et al.; Passive sampling of ambient, gaseous air pollutants: an assessment from an ecological perspective, Environmental Pollution, (Jan. 2000) 107 (1) ,pp. 31-45 2 page printout of PubMed abstract provided only.

(Continued)

*Primary Examiner* — Thomas P Noland
(74) *Attorney, Agent, or Firm* — Gifford, Krass, Sprinkle, Anderson & Citkowski, P.C.

(57) ABSTRACT

A novel multi-gas passive sampler is described, whereby different collection media are packed into one passive sampler to collect a variety of air pollutants (or groups of air pollutants) at the same time. By comparison with known commercially available passive samplers—in which only a single collection medium is used to collect a single air pollutant of or group of air pollutants—the MGPS is more cost effective, convenient to use and more environment-friendly.

9 Claims, 8 Drawing Sheets two pollutants

OTHER PUBLICATIONS

Lewis, R.G, et al.; Thermally desorbable passive sampling device for volatile organic chemicals in ambient air, Analytical Chemistry, (1985), p. 214 only of 214-219 provided.

Tang, H. et al; A New Passive Sampling System for Monitoring SO2 in the Atmosphere, FACT, (1997), 1: pp. 307-314, 2 page printout of Wiley InterScience abstract only provided.

Tang, H. et al.; A new all season passive sampling system for monitoring ozone in air, Environ. Monit. Assess. (2000); 65 1-2, 129-137; 1 page Wiley InterScience abstract provided only.

Tang, H. et al.; A new all season passive sampling system for monitoring H2S in air; The Scientific World, 2, 155-168, Jan. 2002, 1 page MEDLINE abstract provided only.

Uchiyama, S. et al; A scientific diffusion sampler for the determination of the volatile organic compounds in ambient air, Atmospheric Environment, (Jun. 1999), vol. 33, No. 12, pp. 1913-1920, 3 page printout of ScienceDirect abstract only provided.

Tang H. et al; "A New All Season Passive Sampling System for Monitoring Ozone in Air" Environmental Monitoring and Assessment 65: 129-137, 2000, p. 129 only provided.

\* cited by examiner

---Prior Art---

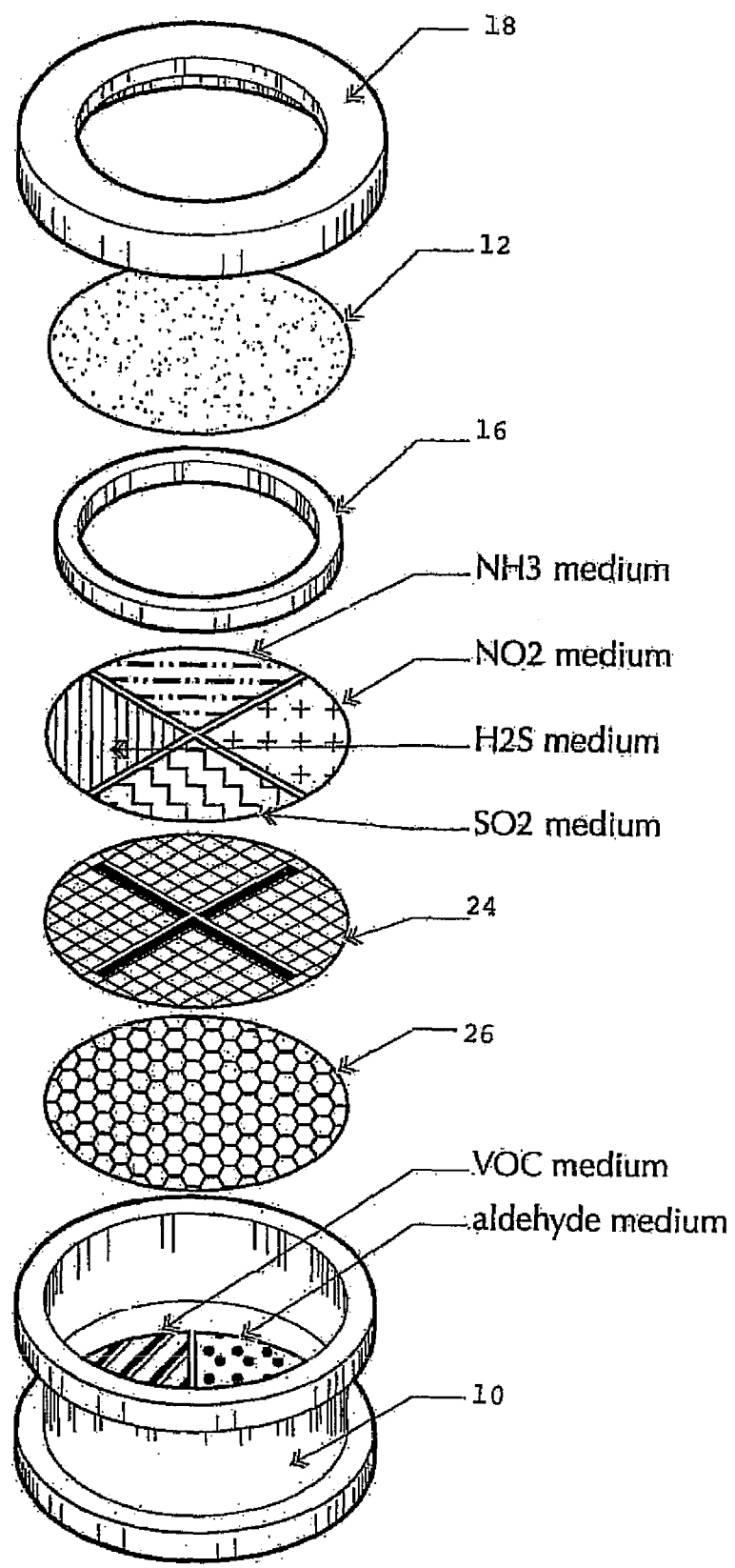
Figure 3 - seven pollutants

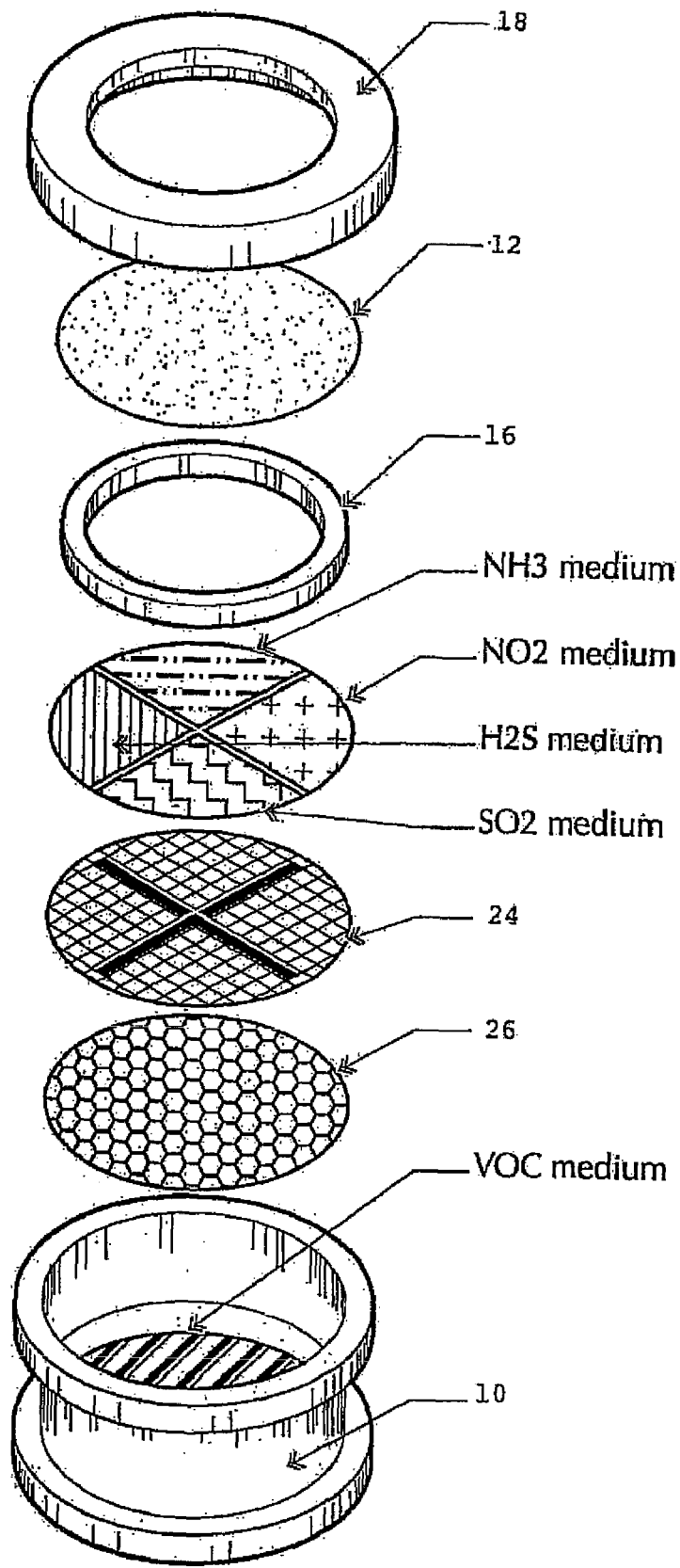
Figure 4 - six pollutants

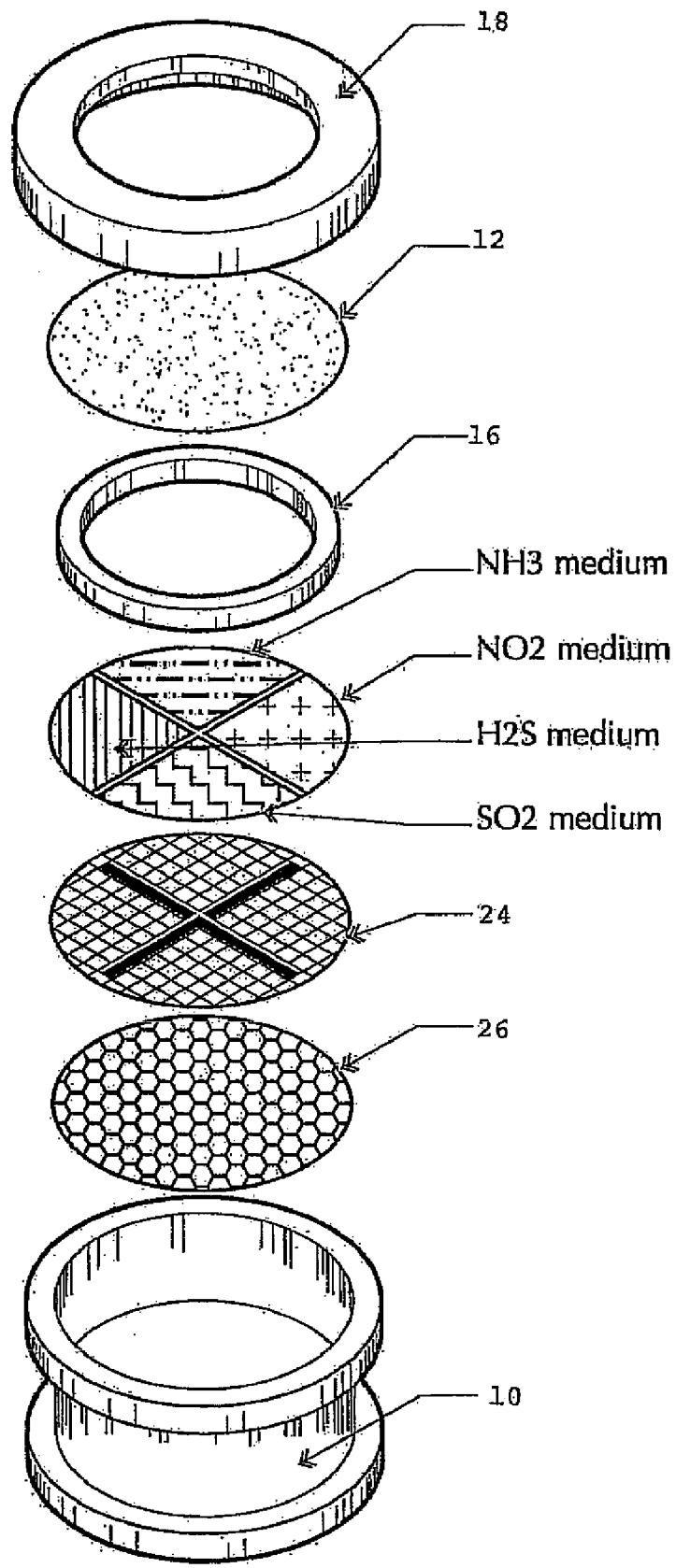
Figure 5 - five pollutants

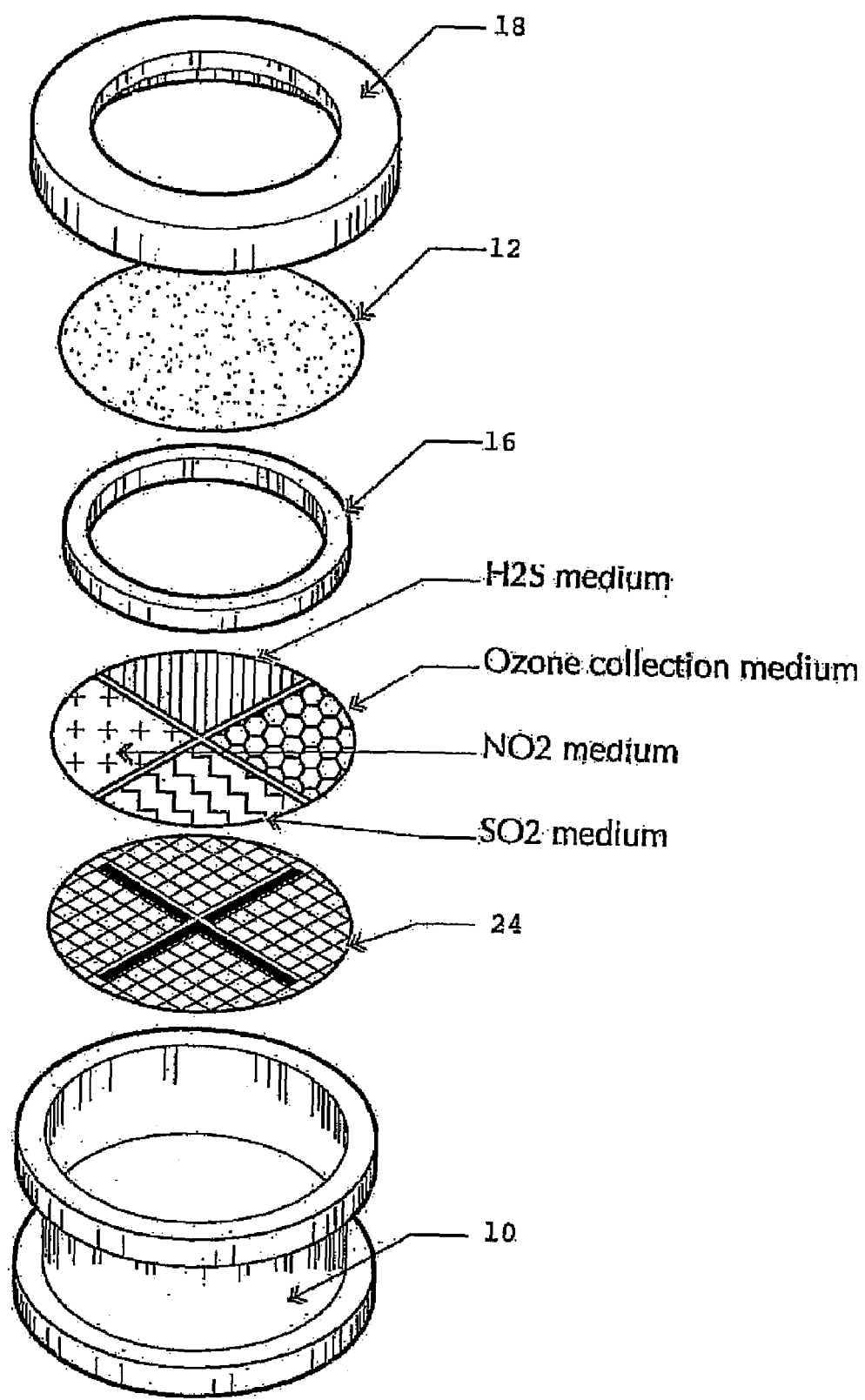
Figure 6 - four pollutants

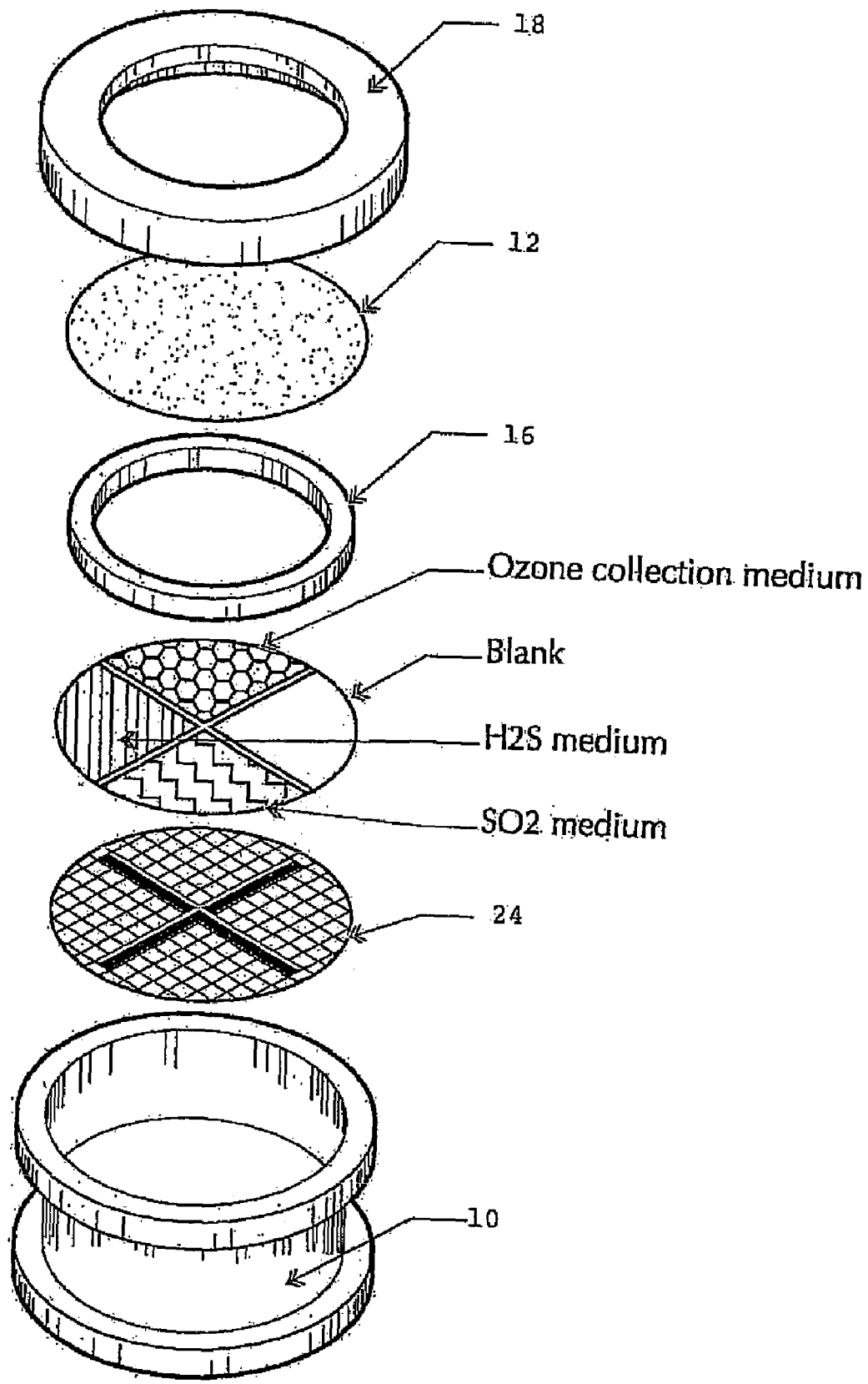
Figure 7 - three pollutants

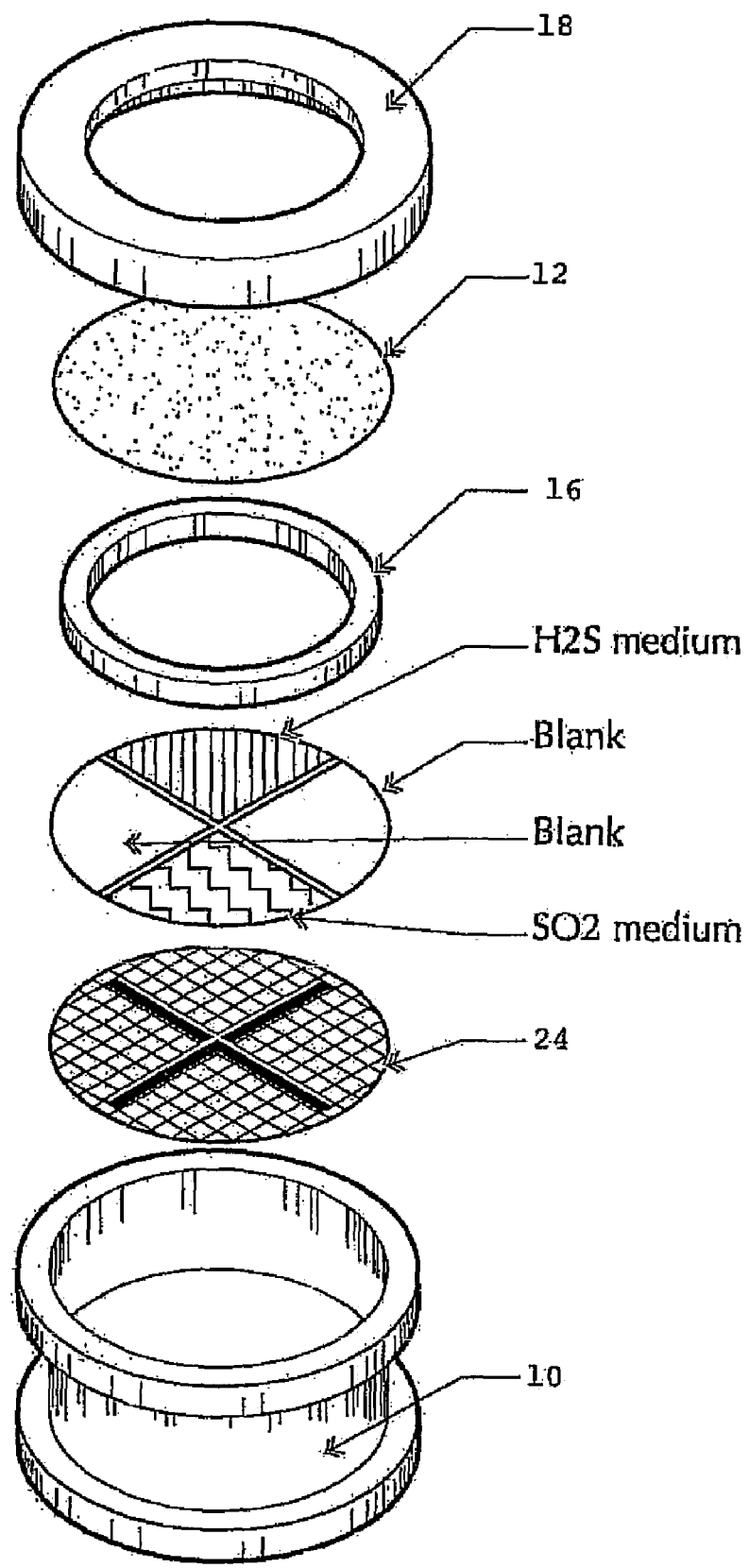
Figure 8 - two pollutants

US 7,980,147 B2

MULTIGAS PASSIVE SAMPLER

RELATED APPLICATIONS

This application is a continuation-in-part of U.S. patent application Ser. No. 12/143,260 filed on Jun. 20, 2008 entitled MULTIGAS PASSIVE SAMPLER which claims priority of U.S. provisional application No. 60/945,119 filed on Jun. 20, 2007 and also entitled MULTIGAS PASSIVE SAMPLER.

FIELD OF THE INVENTION

The invention relates to passive sampling, more particularly technologies for passively sampling multiple air pollutants simultaneously. A group of air pollutants that are collected on the same collection medium, such as volatile organic compounds (VOC), aldehyde and ketone (ANK) etc., is considered as a single air pollutant in the present specification and claims.

BACKGROUND OF THE INVENTION

There is great scientific and social interest in monitoring air pollutants indoors and outdoors. Many monitoring technologies for air pollutants have been developed and subsequently improved in the past few decades. Generally speaking, these technologies can be classified as either integrative collection or real-time analytical technologies. Both technologies can be further divided into two categories: active and passive methods.

Active methods directly pump air through collection or analytical devices to collect or analyze air pollutants. Therefore, electrical power is typically required. A passive (or diffusive) sampler is a device which is capable of taking samples of gas or vapor pollutants from air at a rate controlled by a physical process such as diffusion through a static air layer or permeation through a membrane and does not involve actively drawing or impelling the air through the sampler. Passive samplers are generally simple in structure and do not require electricity. Therefore, passive samplers are relatively cost-effective and convenient to use.

A number of different passive samplers have been developed and are in current commercial use. Passive sampling and systems for carrying out passive sampling are described, inter al, in the following documents:

Koutrakis, P.; Wolfson, J. M., Bunyaviroch, A., Froehlich, S. E., Hirono, K., and Mlik, J. D., (1993), "Measurement of ambient ozone using a nitrite coated filter", *Anal. Chem.*, 65, 209-214.

Krupa, S. and Legge, A., (2000), "Passive sampling of ambient, gaseous air pollutants: an assessment from an ecological perspective", *Environmental Pollution*, 107, 31-45.

Lewis, R. G.; Mulik, J. D.; Coutant, R. W.; Wooten, G. W.; Mcmillin, C. R.; (1985), "Thermal desorbable passive sampling device for volatile organic chemicals in ambient air", *Analytical Chemistry*, 57, 214-219.

3M, VOC passive sampler, www.3m.com

Ogawa & Company USA, http://ogawansa.com

Tang, H.; Brassard, B.; Brasssard R.; Peake, E.; (1997), "A New Passive Sampling System for Monitoring SO$_2$ in the Atmosphere", *FACT*, 1(5), 307-315.

Tang, H.; Lau, T.; Brassard B.; Cool, W., (1999), "A New All-season Passive Sampling System for Monitoring NO$_2$ in Air", *FACT*, 6, 338-345.

Tang, H. and Lau, L., (2000) "A new all season passive sampling system for monitoring ozone in air", *Environ. Monit. Assess.* 65/1-2, 129-137.

Tang, H.; Sandeluk, J,; Lin L,; and Lown W.; (2002) "A new all season passive sampling system for monitoring H2S in air", *The ScientificWorld*, 2, 155-168.

Uchiyama, S.; Asai, M.; Hasegawa, S.; (1999), "A scientific diffusion sampler for the determination of the volatile organic compounds in ambient air", *Atmospheric Environment*, 33, 1913-1920.

All of the above-listed documents are hereby incorporated by reference for their teachings in connection with passive sampling systems. Of these, Krupa and Legge (2000) summarize the available passive samplers into different types, such as badge (3M), diffusion tube with filter absorption (Ogawa) or solid absorption (Uchiyama et al. 1999), and adsorption cartridge (Lewis et al. 1985) etc.

All of the passive samplers described in publications such as those identified above are used to collect a single air pollutant such as $SO_2$, $NO_2$, $NO_x$, $H_2S$, $O_3$, $NH_3$, VOC, ANK etc. As a practical matter, however, in many studies it is necessary to monitor several air pollutants in replication. Thus, a great number of passive samplers and rain shelters are needed at each location making for a cumbersome and expensive system and tedious set-up and collection operation.

SUMMARY OF THE INVENTION

With a view to overcoming these economic and ecological disadvantages of known passive sampling systems, I have provided a multi-gas passive sampler (MGPS) in which a number of different collection media are systematically packed into a single passive sampler to collect a variety of different air pollutants (or groups of air pollutants) at the same time. In preferred embodiments, a passive sampler according to the invention comprises the selected different collection media, a diffusion barrier for allowing air into the sampler in a controlled manner and an arrangement of support screens and spacer rings, respectively for holding the sample media as separated sampler elements and for holding the sampler elements in parallel spaced alignment.

DESCRIPTION OF THE DRAWINGS

FIG. 3 is an exploded schematic view of a passive sampler according to the present invention for the simultaneous sampling of seven atmospheric pollutants;

FIG. 4 is an exploded schematic view of a passive sampler according to the present invention for the simultaneous sampling of six atmospheric pollutants;

FIG. 5 is an exploded schematic view of a passive sampler according to the present invention for the simultaneous sampling of five atmospheric pollutants;

FIG. 6 is an exploded schematic view of a passive sampler according to the present invention for the simultaneous sampling of four atmospheric pollutants;

FIG. 7 is an exploded schematic view of a passive sampler according to the present invention for the simultaneous sampling of three atmospheric pollutants; and FIG. 8 is an exploded schematic view of a passive sampler according to the present invention for the simultaneous sampling of two atmospheric pollutants.

DETAILED DESCRIPTION OF THE INVENTION

Figure 1:
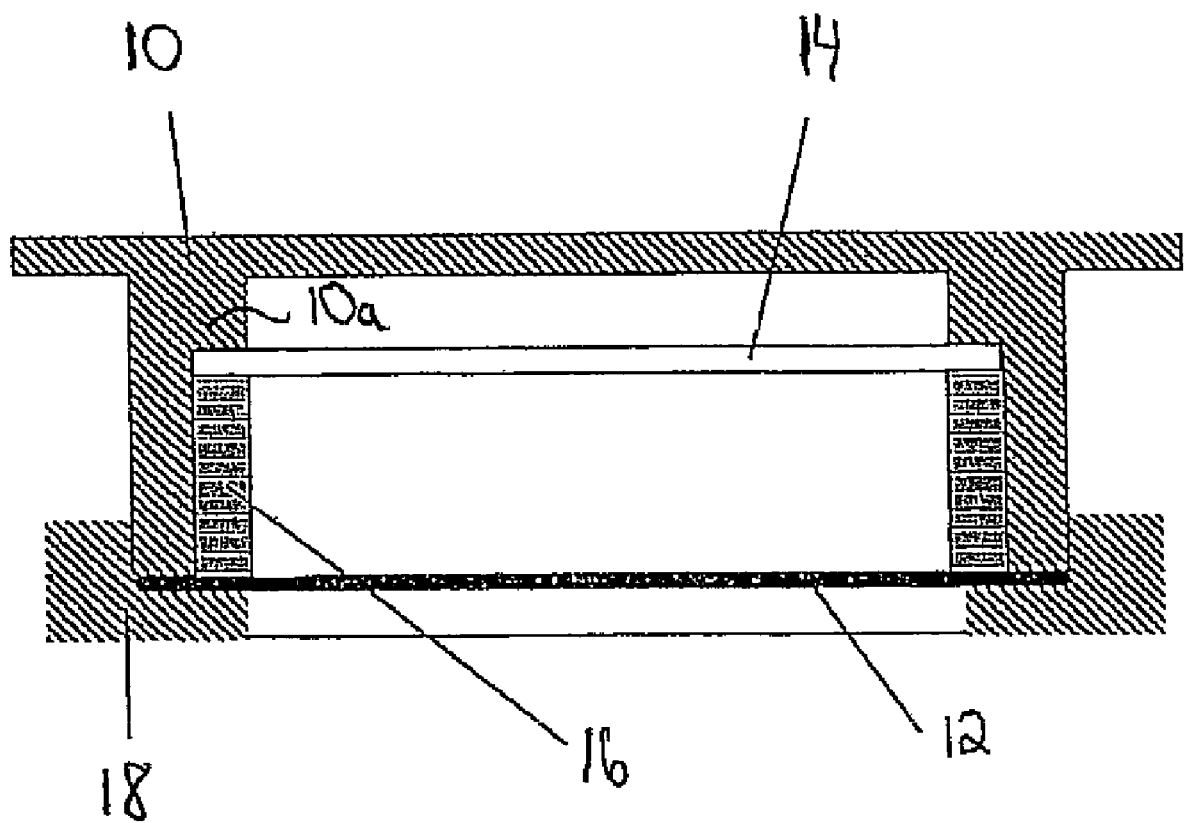
FIG. 1 is a known single-medium passive sampler which may be adapted for multi-gas sampling according to the present invention.

The invention resides in the number and sequencing of multiple air pollution collection media. These can be, as appropriate to the specific pollutants to be sampled, treated granular materials such as silica gel or activated charcoal supported by specially treated planar screens, fine particles of reactive sorbent on an air-permeable substrate, or chemically-treated filters.

The invention may be carried out by simple modification of known commercially-available passive samplers, which use a single collection medium to collect a single air pollutant or group of air pollutants, which contains a diffusion barrier (filter) and a spacer ring, and which affords enough space to host at least two support screens and several layers of collection medium.

One such passive sampler is that designed by Tang et al., described in four of the above-listed documents incorporated by reference.

The Tang et al. passive sampler comprises a generally cylindrical body 10 whose open end, in use, is covered by a diffusion barrier 12 in single sampling medium (sampler) 14 is shown which is spaced from diffusion barrier 12 by support ring 16 and held in position between ring 16 and annular ledge 10a on body. Support ring 16 can also be considered a spacer ring. Diffusion barrier 12 is peripherally sealed to the open end of the sampler body and to the support ring by removable sampler cover 18.

Figure 2:
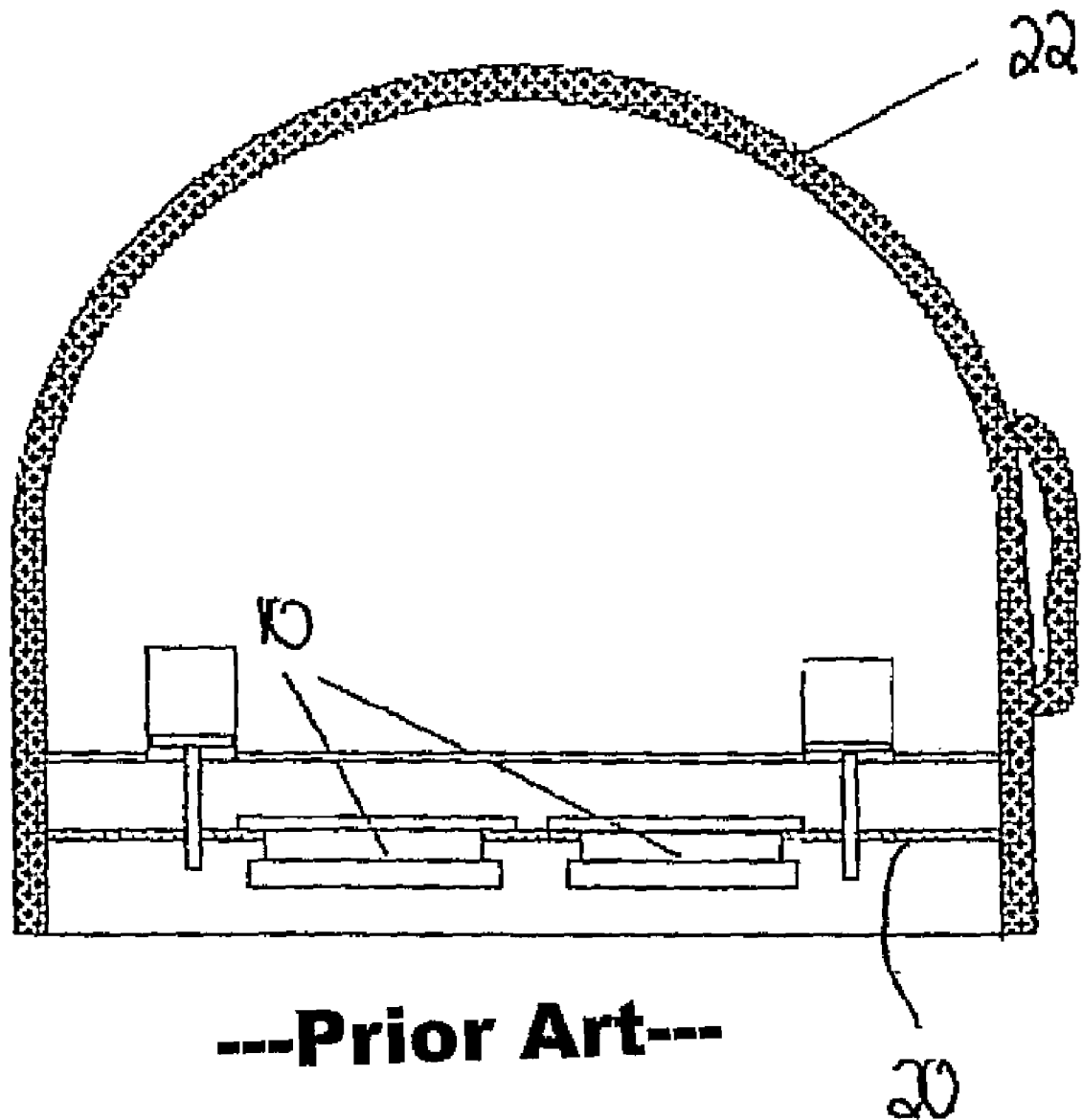
FIG. 2 is a schematic drawing of a passive sampling system using three passive samplers according to FIG. 1 and having a protective rain shelter.

FIG. 2 schematically illustrates a passive sampler system employing three samplers (only two visible) of the kind indicated in FIG. 1, maintained in a horizontal arrangement by support means 20 and protected by a dome-shaped rain shelter 22 for outdoor use.

As noted above, for many purposes it is necessary to monitor simultaneously a number of different air pollutants, so the number of samplers and rain shelters required can be considerable. For example, if seven air pollutants are required to be monitored at the same time and at the same location—in triplicate for meaningful averaging of measurements—then seven rain-shelters and twenty-one passive samplers are called for, using current technology.

FIGS. 3-8 illustrate examples of multi-gas passive samplers (MGPS) according to the present invention. The passive sampler body 10, pollutant collection media with support screens 24, support ring 12 and sampler cover 18 are shown in exploded view, in the sequential order of their assembly. Once assembled the sampler is inverted with the covers 18 disposed to the underside, as in the orientation of FIG. 1.

FIGS. 3-8 illustrate MGPS according to the present invention. FIG. 3 illustrates an MGPS assembly for seven pollutants ($SO_2$, $NO_2$, $H_2S$, $O_3$, $NH_3$, VOC and ANK); FIG. 4 for six pollutants ($SO_2$, $NO_2$, $H_2S$, $O_3$, $NH_3$ and VOC); FIG. 5 for five pollutants ($SO_2$, $NO_2$, $H_2S$, $O_3$ and $NH_3$); FIG. 6 for four pollutants ($SO_2$, $NO_2$, $H_2S$ and $O_3$); FIG. 7 for three pollutants ($SO_2$, $H_2S$ and $O_3$); and FIG. 8 for two pollutants ($SO_2$ and $H_2S$).

In the drawings, in a number of instances, a given circular layer of sampling medium (hereinafter referred to as a "sampler element") will consist of two or more separate media arranged in sectors. Ozone collection medium, sulfur dioxide collection medium, hydrogen sulfide collection medium, nitrogen dioxide collection medium and ammonia collection medium are referred to by the abbreviations as OCM, SCM, HSCM, NCM and ACM. "VOCM" refers to the medium for sampling volatile organic compounds, collectively treated as a single air pollutant. "ANKM" similarly designates an aldehydes and ketones collection medium.

In FIG. 4 (six pollutants) it will be seen that the first layer of medium after the diffusion barrier has equiangular segments of $NH_3$ medium, $NO_2$ medium, $H_2S$ medium and $SO_2$ medium. The contiguous porous screen 24 is partitioned into four corresponding sectors, each of which can be provided with an appropriate identification symbol for matching up with the segments of $NH_3$ medium, etc. One or two sectors may be left open, if only three or two media segments are used in the first layer [see FIGS. 7 and 8].

The MGPS for seven air pollutants is shown in FIG. 3. The bottom of the passive sampler is packed with a bag VOCM of commercially-available activated charcoal for sampling VOC and a bag ANKM of commercially-available DNPH-coated silica gel for sampling aldehydes and ketones. Above the bags VOCM and ANKM is an ozone collection filter 26, which also acts as an ozone scrubber to protect active organic compounds such as formaldehyde from reacting with ozone.

In the loaded passive samples of FIG. 3, marked four-part screen 24 is installed above the ozone collecting medium to separate the first layer collection media from the ozone collection filter. The marks on screen 24 are used to identify the four collection media ($SO_2$, $NO_2$, $H_2S$, and $NH_3$) are packed above adjacent screen 24. A small spacing (0.5 mm) is required between each pair of collection media in order to avoid cross-contamination and cross-interference.

For efficient and accurate operation of the passive sampler there are a number of constraints to the choices of collection media and to the order in which the collection media must be assembled in the sampler body. One such is the need to ensure that an upstream collection medium does not scrub out a pollutant that is be collected by a downstream medium.

Another constraint related to ensuring that the collection media do not contaminate each other, particularly as one pollutant may act, either by itself or in concert with other chemicals, as the collection medium for a second pollutant.

Finally, and most generally a given pollutant may be collected by a number of different collection media and therefore, the order of the collection media may depend on the choices of media used to collect the pollutants. The sequential order of the collection media may be of critical importance, depending on the particular group of pollutants for which sampling is to occur. Most air pollutant collection media are coated with chemicals. For example, say ozone, sulfur dioxide and hydrogen sulfide are to be sampled. If the ozone collection medium (OCM) is chosen to be coated with nitrite and sodium carbonate (Koutrakis et al. 1993), the sulphur dioxide collection medium (SCM) is chosen to be coated with carbonate and the hydrogen sulfide collection medium (HSCM) is chosen to be coated with silver nitrate and nitric acid, then the SCM and the HSCM may not be placed downstream of the OCM because the sodium carbonate in the OCM will react with (scrub out) $SO_2$ and $H_2S$ before they reach their collection media (FIGS. 3-5).

In use of MGPS, according to the invention, care must be taken to avoid cross-contamination of media. The nitrogen dioxide collection media (NCM) react with $NO_2$ and generate nitrite. Because the OCM are coated with nitrite, the NCM and OCM cannot contact each other. In order to avoid contamination, the NCM should not be installed near the OCM (FIG. 4). Nitric acid in the HSCM can react with basic compounds. Therefore any collection substrate coated with basic compound such as SCM, NCM, and OCM etc. must avoid contact with the HSCM.

Tables 1 and 2 compare the relative amounts of inputs used for NPS and MGPS by using passive samplers and rain-shelters designed by Tang et al (1997) and collecting in triplicate. Table 1 compares the savings for four pollutants ($SO_2$, $NO_2$, $H_2S$, and $O_3$) and Table 2 compares the savings for two pollutants ($SO_2$ and $H_2S$).

TABLE 1

Comparison of four air pollutants collected
in triplicate by NPS and MGPS

| ITEM | No. for NPS | No. for MGPS | No. Saved | % Saved |
|---|---|---|---|---|
| Rain shelter | 4 | 1 | 3 | 75 |
| Passive body | 12 | 3 | 9 | 75 |
| Diffusion Barrier | 12 | 3 | 9 | 75 |
| Collection filter | 12 | 3 | 9 | 75 |
| Chemicals* | 12 | 3 | 9 | 75 |
| Waste generated** | 12 | 3 | 9 | 75 |
| Field installation | 12 | 3 | 9 | 75 |
| Average | | | | 75 |

*1 unit of chemicals equals the total amount of chemicals used per collection medium. As the number of units of chemicals used is perfectly correlated to the number of filters used, 12 units of chemical are used for NPS; only 3 are used for MGPS.
**1 unit of waste generated equals the total extraction volume used per collection medium. As the number of units of waste generated is perfectly correlated to the extraction volumes used per filter, multiplied by the number of filters used, 12 units of waste are generated by NPS; but only 3 units are generated in MGPS.

TABLE 2

Comparison of two air pollutants collected
in triplicate by NPS and MGPS

| ITEM | No. for NPS | No. for MGPS | No. Saved | % Saved |
|---|---|---|---|---|
| Rain shelter | 2 | 1 | 1 | 50 |
| Passive body | 6 | 3 | 3 | 50 |
| Diffusion Barrier | 6 | 3 | 3 | 50 |
| Collection filter | 6 | 1.5 | 4.5 | 75 |
| Chemicals* | 6 | 1.5 | 4.5 | 75 |
| Waste generated** | 6 | 1.5 | 4.5 | 50 |
| Field installation | 6 | 3 | 3 | 61 |
| Average | | | | 50 |

* & **See table 1

In addition to material savings, labor savings also flow in MGPS in terms of manufacture, field installation and change-out, labeling and handling. As well, infrastructure materials, i.e. rain shelters, supporting structures, etc. are also economized through MGPS.

Generally, the passive air sampling rates in the MGPS can be derived following the procedures published by Tang et al (1997, 1999, 2000, and 2002). Tables 3 and 4 list field studies by using NPS and MGPS for two air pollutants ($SO_2$ and $H_2S$) and four air pollutants ($SO_2$, $NO_2$, $O_3$ and $H_2S$) separately. It can be found that the pollution concentrations obtained by both NPS and MGPS were very close.

TABLE 3

Concentrations comparison obtained
by NPS and MGPS for $SO_2$ and $H_2S$

| Parameter | NPS ppb | MGPS ppb | Error %* | Notes |
|---|---|---|---|---|
| $SO_2$ | 4.0 | 3.9 | 2.5 | |
| $H_2S$ | 0.45 | 0.49 | 9 | |

*The number is obtained as following: (ppb NPS − ppb MGPS)*100/ppb NPS

TABLE 4

Concentrations comparison obtained by
NPS and MGPS for $SO_2$, $NO_2$, $O_3$ and $H_2S$

| Parameter | NPS ppb | MGPS ppb | Error %* | Notes |
|---|---|---|---|---|
| $SO_2$ | 4.0 | 3.7 | 8 | |
| $H_2S$ | 0.45 | 0.44 | 2 | |
| $NO_2$ | 17.1 | 16.7 | 2 | |
| $O_3$ | 50.2 | 48.3 | 4 | |

*The number is obtained as following: (ppb NPS − ppb MGPS)*100/ppb NPS

In one of several projects using the MGPS according to the invention, four stations were located in Fort McMurray northern Alberta to monitor $SO_2$, $NO_2$ and $H_2S$. Table 5 below lists results for January 2008 which were found to be very close to historical data measured in a nearby air monitoring station equipped with continuous analyzers. For example, the average $NO_2$ concentration over the three years preceding January 2008 was about 11 ppb. We found the average concentration in stations 1 and 4 in January was about 10 ppb. Stations 2 and 3 are closed to the major air pollution source, where the $NO_2$ concentrations were about 14 ppb.

TABLE 5

Monitoring results for January 2008 in FMNA

| Station ID | $SO_2$ ppb | $NO_2$ ppb | $H_2S$ ppb |
|---|---|---|---|
| 1 | 1.4 | 10.2 | 0.8 |
| 2 | 1.9 | 13.5 | 0.9 |
| 3 | 3.0 | 14.0 | 1.9 |
| 4 | 1.7 | 9.4 | 0.7 |

In summary, with our development of multigas passive sampling systems (MGPS) a passive sampling technology has been provided which is environmentally friendly, more cost effective, more convenient to use and more accurate than the prior art discussed above. The MGPS is a new and useful in the air monitoring sector for indoor and ambient atmosphere.

Although the invention has been illustrated and described herein with respect to particular preferred embodiments, it will be understood that other equivalent structures and materials could be used to embody applicant's inventive concept of providing a passive sampler with a plurality of sampling media for the simultaneous collection of a number of different air pollutants. Accordingly, the invention to be protected is intended to be defined by the literal language of the claims and the equivalent thereof.

I claim:

1. A multigas passive sampler, comprising:
    (i) a body having an open end and a closed end;
    (ii) a plurality of installable and removable sampler elements carrying selected sampler media inside said body, for sequentially collecting a variety of pollutants from air entering said body through the open end thereof, at least two selected sampler media being sectors of a single sampler element; and
    (iii) a diffusion barrier covering said open end of the body and at least one spacer ring for maintaining fixed spaces among said plurality of installable and removable sampler elements.

2. A multigas passive sampler according to claim 1, wherein said body is cylindrical and said sampler elements are of circular contour coaxial with said body.

3. A multigas passive sampler according to claim 1, further comprising an annular cover ring for holding said diffusion barrier over the opening into said body.

4. A multigas passive sampler according to claim 1, further comprising a porous support screen for said single sampler element, said support screen being partitioned into sectors corresponding to and contiguous with said at least two of said sampler media.

5. A multigas passive sampler according to claim 4, wherein each sector of said screen is provided with a visible marking to correspond to its associated sector of the single sampler element.

6. A multigas passive sampler according to claim 1, wherein each sampler element comprises a filter chemically treated with a selected sampler medium.

7. A multigas passive sampler according to claim 1, wherein said single sampler element is made up of four sectors respectively holding ammonia sampler medium, nitrogen dioxide sampler medium, hydrogen sulfide sampler medium and sulfur dioxide sampler medium.

8. A multigas passive sampler according to claim 7 further comprising an ozone sampler element.

9. A multigas passive sampler according to claim 7 further comprising a sampler element for volatile organic compounds and for aldehyde and ketone.

* * * * *